United States Patent
Lee et al.

(10) Patent No.: US 7,887,489 B2
(45) Date of Patent: Feb. 15, 2011

(54) SYSTEM AND METHOD FOR DETECTING SLEEPINESS

(75) Inventors: Jae Jin Lee, Daejeon (KR); Chung Hwan Kim, Daejeon (KR); Min Gun Kim, Daejeon (KR)

(73) Assignee: Telecommunication & Electronics Inc., Daejeon (KR)

( * ) Notice: Subject to any disclaimer, the term of this patent is extended or adjusted under 35 U.S.C. 154(b) by 0 days.

(21) Appl. No.: 12/520,246

(22) PCT Filed: Aug. 29, 2008

(86) PCT No.: PCT/KR2008/005068
§ 371 (c)(1),
(2), (4) Date: Mar. 3, 2010

(87) PCT Pub. No.: WO2009/142360
PCT Pub. Date: Nov. 26, 2009

(65) Prior Publication Data
US 2010/0234741 A1    Sep. 16, 2010

(30) Foreign Application Priority Data
May 22, 2008    (KR) .................. 10-2008-0047481

(51) Int. Cl.
*A61B 5/02* (2006.01)
(52) U.S. Cl. .............. 600/484; 600/500; 600/508; 600/483
(58) Field of Classification Search .......... 600/484, 600/493, 500, 508, 509, 483; 340/573.1, 340/575, 576
See application file for complete search history.

(56) References Cited

U.S. PATENT DOCUMENTS
7,206,631 B2 * 4/2007 Kawachi et al. ............. 600/519
2005/0143667 A1 6/2005 Park et al.
2009/0261979 A1 * 10/2009 Breed et al. ................. 340/576

FOREIGN PATENT DOCUMENTS
JP    11-128177 A    5/1999

* cited by examiner

*Primary Examiner*—Charles A Marmor, II
*Assistant Examiner*—Michael D'Angelo
(74) *Attorney, Agent, or Firm*—Drinker Biddle & Reath LLP

(57) ABSTRACT

The present invention relates to a drowsiness detection method. A heartbeat signal and a breathing signal are detected by exploiting together a scheme and an optical system scheme. The detected signals are applied to respective amplification units, noise signals are eliminated from the detected signals, and noise-free signals are amplified. The amplified signals are applied to a central processing unit, signal processing is processed on the signals, and processed signals are combined. The combined signal is counted, and a warning sound, voice message or vibration is output in a case where a value, obtained by subtracting a counted output value monitored one minute before a current time, from a counted output value monitored two minutes before the current time, falls within a detection range and where, with a passage of time, the value falling within the detection range is successively detected from two to ten times.

15 Claims, 4 Drawing Sheets

SYSTEM AND METHOD FOR DETECTING SLEEPINESS

CROSS REFERENCE TO RELATED APPLICATIONS

This application is the U.S. national phase of the International Patent Application No. PCT/KR2008/005068 filed Aug. 29, 2008, which claims the benefit of Korean Application No. 10-2008-0047481 filed May 22, 2008, the entire content of which is incorporated herein by reference.

BACKGROUND

The present invention relates, in general, to a drowsiness detection method. Various embodiments of the invention relate to a drowsiness detection method which can detect the heartbeat signal and breathing signal of a user without coming into direct contact with the target body of the user, can count a signal output value through signal amplification and processing of the detected signals, and can output a warning sound, voice message or vibration through an output unit in the case where a value, obtained by subtracting a counted output value which was monitored one minute before a current time, from a counted output value which was monitored two minutes before the current time, falls within a range from 2 to 10, or from −2 to −10 and where, with the passing of time, the value falling within the range from 2 to 10 or from −2 to −10 is successively detected from two to ten times within the same range.

Generally, heart rate monitors for measuring biological signals such as the heartbeat of a human body are classified into contact and non-contact types.

The most popular one of contact type monitors is a monitor using a pulse oximeter, and is implemented using a method of putting a probe on the finger of a measurement target user and detecting biological information, such as blood oxygen saturation, pulse rate, and pulse amplitude. Further, another contact type monitor uses an electrocardiograph, and is configured to attach electrodes to body regions such as the breast, wrist and ankle, measure signals and extract heartbeat information.

Such a conventional heartbeat detection method is problematic in that, since it basically uses a method of attaching a monitor or a plurality of electrodes to a part of the body of a measurement target user or putting a band with a monitor attached thereto on the part of the body, the user feels aversion and inconvenience, and in that biological signals such as a heartbeat cannot be measured unless direct contact is made with a target body.

Further, as other methods, there are conventional technologies proposed to detect biological signals such as a heartbeat in a non-contact manner. One of the conventional technologies is a patent disclosed in Korean Patent Appln. No. 10-2006-0019267 which was registered and is entitled "Remote Biological Information Detection Apparatus and Application Apparatus Thereof". Such a patent relates to a method of measuring biological information using the principle of a Doppler radar, and is configured to obtain biological information from the variation in signals generated as a result of the motion of the internal organs of a human body.

SUMMARY

FIG. 1 is a block diagram showing a conventional heartbeat measurement apparatus using the principle of a Doppler radar. Referring to FIG. 1, a remote biological information detection apparatus using the principle of a Doppler radar is configured such that certain frequency signals output from a signal generator are divided by a coupler, some signals are incident on a target body through a transmission antenna, most of radio wave signals incident on the target body are reflected from the skin, and some of the incident radio wave signals penetrate into the skin and are then reflected and output from the internal organs of the body. The signals reflected and output from the target body are received through a reception antenna and are amplified by a Low-Noise Amplifier (LNA), and the amplified signals are mixed with the signals of the signal generator, which are output from the coupler, by a frequency mixer. The output signal of the frequency mixer is amplified and is processed by a low-pass filter and a digital signal processing unit.

However, the conventional technology is problematic in that, at the time of measuring biological signals such as a heartbeat signal and a breathing signal, measurement is performed without considering the influence of the motion of other regions of a target body, thus making it impossible to accurately measure biological signals due to signal transformation attributable to the motion of the human body.

Conventional drowsiness detection sensors are classified into an earring-type sensor and a glasses-type sensor configured such that an accelerometer is attached to an earring or glasses and a warning sound is generated when a portion of the attachment becomes inclined at an angle of 10 degrees or greater.

However, the earring-type or glasses-type sensor is disadvantageous in that a user must personally wear the earring or the glasses, and in that, when the user turns his or her head to talk with a neighboring person or hangs down his or her head toward the lower portion of a steering wheel so as to shift a gear, a warning sound is generated.

Accordingly, an object of the present invention to solve the above problems occurring in the prior art is to provide a drowsiness detection method which successively measures the heart rate and the number of breaths of a user, counts a normal heart rate, compares the counted value with a counted value, obtained when a heart rate and the number of breaths are reduced due to the occurrence of drowsiness, through subtraction, and notifies the user of any danger by outputting a warning sound, voice message or vibration when the user is determined to be drowsy.

In order to accomplish the above object, various embodiments of the present invention provide a drowsiness detection method comprising a first step of detecting a heartbeat signal and a breathing signal without making direct contact with a target body by exploiting together a scheme using a principle of a Doppler radar and an optical system scheme using a light source/photodetector so that a heartbeat can be detected when a human body is moving, a second step of applying the signals, detected by the scheme using the principle of the Doppler radar and the optical system scheme using the light source/photodetector to respective amplification units, eliminating noise signals from the detected signals, respectively, and amplifying noise-free signals, a third step of applying signals output at the second step to a central processing unit, performing signal processing on the signals, and combining respective processed signals, and a fourth step of counting an output value output at the third step, and outputting a warning sound, voice message or vibration through an output unit in a case where a value, obtained by subtracting a counted output value which was monitored one minute before a current time, from a counted output value which was monitored two minutes before the current time, falls within a range from 2 to 10, or from −2 to −10 and where, with a passage of time, the value falling within the range from 2 to 10 or from −2 to −10 is successively detected from two to ten times within a same range.

In various embodiments of the present invention, the optical system comprises a filter unit arranged upstream of a photodetection unit and configured to allow only light, having a specific wavelength and a predetermined light source bandwidth, to pass therethrough. The light source bandwidth may be less than 100 nm. The light source may be implemented using a Light Emitting Diode (LED) or a Laser Diode (LD). The light source may use visible, infrared or ultraviolet rays.

In order to accomplish another object, various embodiments of the present invention provide a drowsiness detection method comprising a heart rate monitor including a radar system and an optical system, an amplification unit, a central processing unit and an output unit, wherein the radar system comprises a signal generator for generating specific frequency signals; a coupler for receiving the signals generated by the signal generator and dividing a second signal, which is a reference frequency signal, and a first signal to be radiated to a heart of a target body, and outputting the first and second signals; a transmission antenna for receiving the first signal from the coupler and radiating the first signal to the heart of the target body; a reception antenna for receiving a reflected wave which is returned from the heart of the target body after the first signal has been transmitted through the transmission antenna and has been incident on the heart of the target body; a low-noise amplifier for amplifying a signal received through the reception antenna; a mixer for mixing the second signal output from the coupler with the signal amplified by the low-noise amplifier; and a signal processing unit for amplifying a signal output from the mixer, filtering the amplified signal, converting the filtered signal into a digital signal, and outputting the digital signal, and wherein the optical system comprises a light source unit including a light source for generating light and a light transmission optical system for radiating light to a portion identical to a heart region of the target body to which the signal is radiated by the transmission antenna of the radar system; a photodetection unit including a light reception optical system for detecting a light signal reflected from the target body after being radiated to the target body; a motion signal processing unit for extracting a noise signal attributable to a motion of the target body from the signal detected by the photodetection unit; and a digital signal processing unit for converting the noise signal extracted by the motion signal processing unit into a digital signal and outputting the digital signal, wherein the heart rate monitor further comprises a combiner for eliminating the noise signal output from the digital signal processing unit of the optical system from the signal output from the signal processing unit of the radar system; and a biological signal recognition unit for obtaining biological signals from the combiner, wherein the amplification unit receives signals respectively detected by a scheme using a principle of the Doppler radar and a scheme of the optical system using the light source/photodetector, eliminates noise signals from the detected signals, respectively, and amplifies the noise-free signals, and wherein the central processing unit individually receives signals output from the amplification unit, performs signal processing on the signals, combines the processed signals with each other, counts each of values output from the amplification unit, monitors the output value, and outputs a warning sound, voice message or vibration through the output unit if it is determined as a result of the monitoring that the output value falls within a detection range.

The detection range may be a range in which a value, obtained by subtracting a counted output value which was monitored one minute before a current time from a counted output value which was monitored two minutes before the current time through processing of the central processing unit which counts the output value, falls within a range of 2 to 10 and in which the value falling within the range from 2 to 10 is successively detected from two to ten times with passage of time. The optical system may further comprise a filter unit arranged upstream of the photodetection unit and configured to allow only light, having a specific wavelength and a predetermined light source bandwidth, to pass therethrough. The light source bandwidth may be less than 100 nm. The light source may be implemented using a Light Emitting Diode (LED) or a Laser Diode (LD). The light source may use visible, infrared or ultraviolet rays.

According to the drowsiness detection method, both a method using the principle of a Doppler radar and an optical system scheme using a light source/photodetector are exploited together, so that a noise signal attributable to the motion of a human body is compensated for even when the human body is moving, thus realizing the effect of extracting more accurate biological signals such as heartbeat and breathing signals.

Further, according to the drowsiness detection method, there is an advantage in that various embodiments of the present invention may be mounted on a portable device, an object near a driver (for example, a cushion, a seat, a steering wheel, etc.) or the handle of a bicycle, so that, when a drowsiness signal from the user is detected, a warning sound, voice message or vibration is output through an output unit and is capable of waking the user, thus remarkably reducing the occurrence of traffic accidents attributable to drowsiness, and so that the malfunction of machines attributable to drowsiness is prevented in industrial fields, thus preventing the occurrence of industrial disasters.

DETAILED DESCRIPTION OF THE EMBODIMENTS

Hereinafter, embodiments of a drowsiness detection method according to the present invention will be described in detail with reference to the attached drawings.

Figure 1:
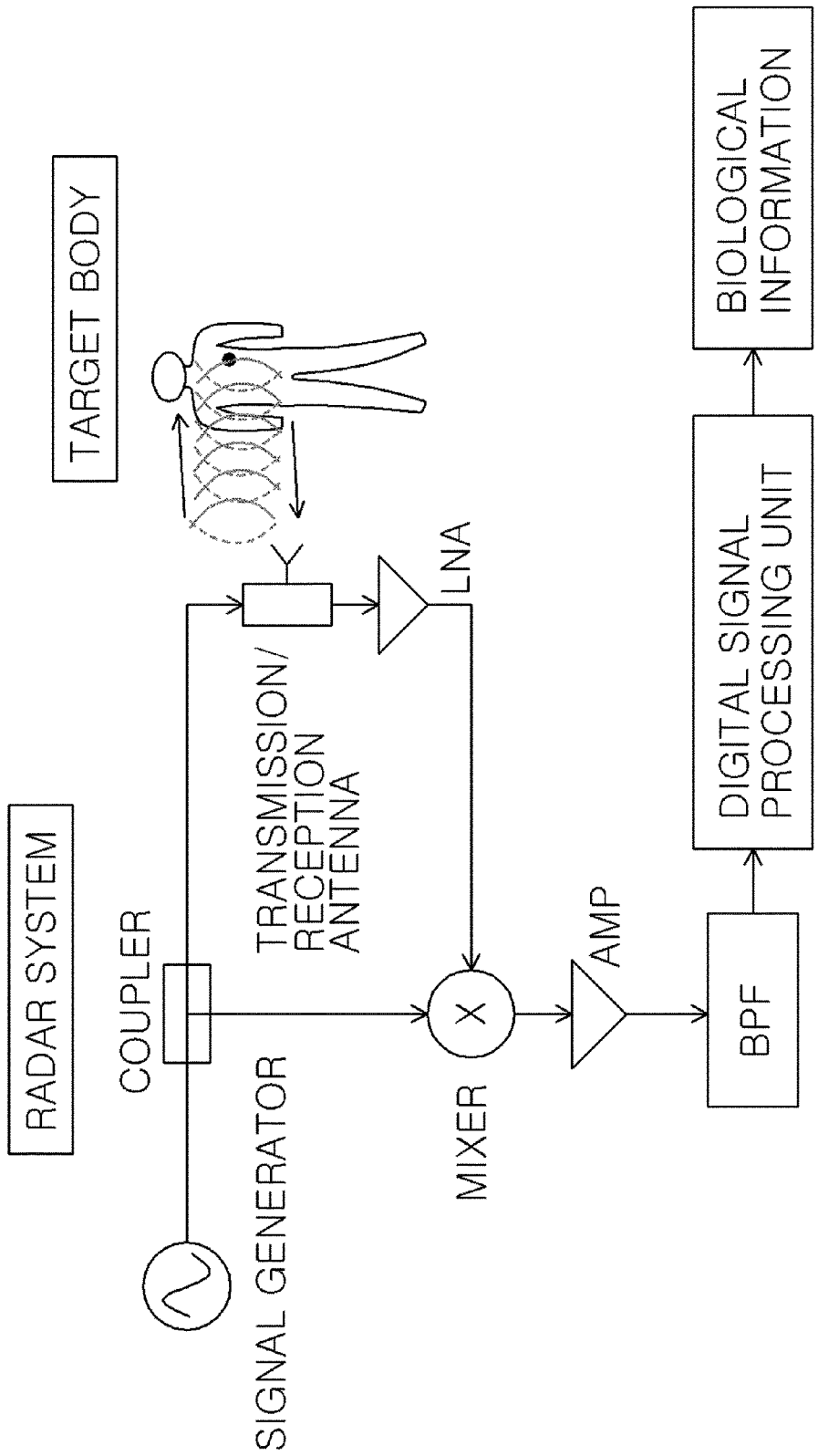
FIG. 1 is a block diagram showing a conventional heartbeat measurement apparatus using the principle of a Doppler radar.
Figure 2:
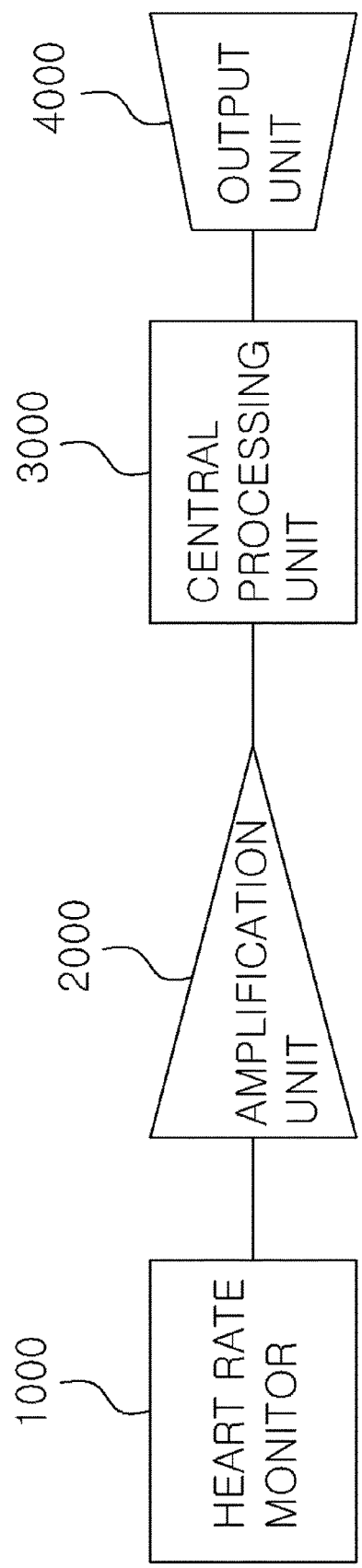
FIG. 2 is a block diagram showing a drowsiness detection apparatus according to an embodiment of the present invention.

As shown in FIG. 2, the drowsiness detection apparatus according various embodiments of the present invention includes a heart rate monitor 1000, an amplification unit 2000, a central processing unit 3000 and an output unit 4000.

The heart rate monitor 1000 exploits together a scheme using the principle of a Doppler radar and an optical system scheme using a light source/photodetector so that a heartbeat can be detected even when a human body is moving, thus detecting a heartbeat signal and a breathing signal without making direct contact with a target body.

The amplification unit 2000 receives signals respectively detected by the scheme using the Doppler radar and the optical system scheme using the light source/photodetector, eliminates noise signals from the detected signals, and amplifies noise-free signals.

The central processing unit 3000 individually receives the output signals of the amplification unit 2000, performs signal processing on the received signals, and combines the processed signals with each other. That is, the central processing unit 3000 counts each of the output signals provided by the amplification unit 200, and outputs a warning sound, voice message or vibration through the output unit 4000 in the case where a value, obtained by subtracting a counted output value which was monitored one minute before the current time, from a counted output value which was monitored two minutes before the current time, falls within a range from 2 to 10, or from −2 to −10 and where, with the passage of time, the value falling within the range from 2 to 10 or from −2 to −10 is successively detected from two to ten times within the same range.

Therefore, the drowsiness detection apparatus successively measures the heart rate and the number of breaths of the user, counts a normal heart rate, compares the counted value with a counted value, obtained when a heart rate and the number of breaths are reduced due to the occurrence of drowsiness, through subtraction, and notifies the user of any danger by generating a warning sound, voice message or vibration when the user is determined to be drowsy.

Figure 3:
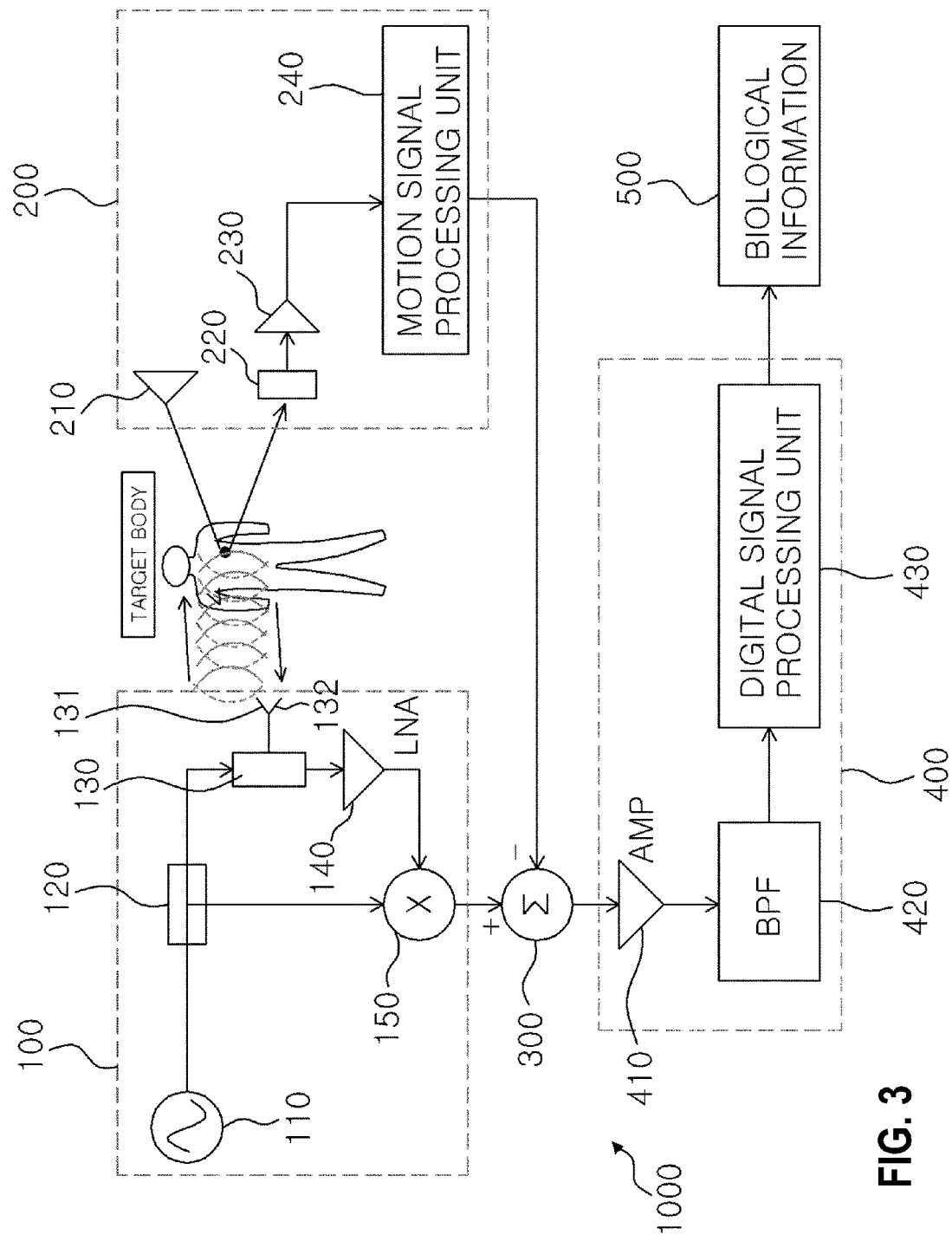
FIG. 3 is a block diagram showing an embodiment of the heart rate monitor of a drowsiness detection apparatus.

FIG. 3 is a block diagram showing an embodiment of the heart rate monitor of the drowsiness detection apparatus.

As shown in FIG. 3, a heart rate monitor 1000 includes a radar system 100, an optical system 200, a combiner 300, and a biological signal recognition unit 500.

The heart rate monitor 1000 includes the radar system 100 and the optical system 200, and further includes the combiner 300 for eliminating a noise signal, which is output from the optical system 200 as a result of the motion of the human body, from the output signal of the radar system 100, a signal processing unit 400 for amplifying the signal output from the combiner 300 using a first amplifier 410, detecting a heartbeat signal and a breathing signal by filtering of the amplified signal using a band pass filter 420, and converting the detected heartbeat and breathing signals into digital signals and outputting the digital signals using a digital signal processing unit 430, and the biological signal recognition unit 500 for obtaining biological signals from the signal processing unit 400.

The radar system 100 includes a signal generator 110, a coupler 120, a transmission/reception converter 130, a low-noise amplifier 140 and a mixer 150.

The signal generator 110 generates and outputs specific frequency signals.

The coupler 120 receives the signals generated by the signal generator 110, divides the signals into a reference frequency signal (hereinafter referred to as a "second signal") and a signal to be radiated to the heart of a target body (hereinafter referred to as a "first signal"), and outputs the first and second signals. Here, the first and second signals may be divided at a predetermined ratio, for example, a ratio of 50:50.

The transmission/reception converter 130 includes a transmission antenna 131 for receiving the first signal from the coupler 120 and radiating the first signal to the heart of the target body, and a reception antenna 132 for receiving a reflected wave which is returned from the heart of the target body after the first signal has been transmitted through the transmission antenna 131 and has been incident on the heart of the target body.

In this case, the low-noise amplifier 140 amplifies the signal received through the reception antenna 132.

The mixer 150 mixes the second signal output from the coupler 120 with the signal amplified by the low-noise amplifier 140, and outputs the mixed signal. The optical system 200 includes a light source unit 210, a photodetection unit 230, and a motion signal processing unit 240.

The optical system 200 may further include a filter unit 220 which allows only light, having a specific wavelength and a predetermined light source bandwidth, to pass therethrough.

The light source unit 210 includes a light source for generating light and a light transmission optical system for radiating the light to the heart region of the target body.

In this case, the light source may be a fluorescent lamp and is not limited to a specific type, but may be preferably implemented using a Light Emitting Diode (LED) or a Laser Diode (LD), and may preferably use visible rays, infrared rays or ultraviolet rays.

Further, the light transmission optical system may be implemented as one system or may be arranged in the form of an array.

Further, light is preferably radiated to a portion identical to the heart region of the target body to which the signal is radiated by the transmission antenna 131 of the radar system 100, that is, a portion having an area similar to the area of the distribution of a radio signal output from the radar system 100.

The photodetection unit 230 includes a light reception optical system for detecting a light signal reflected from the target body after being radiated from the light source unit 210. In this case, the filter unit 220 which allows only light, having a specific wavelength and a predetermined light source bandwidth, to pass therethrough is preferably arranged upstream of the photodetection unit 230. Here, the light source bandwidth is preferably less than 100 nm.

Furthermore, the motion signal processing unit 240 extracts a noise signal attributable to the motion of the target body from the signal detected by the photodetection unit 230. In this case, the motion signal processing unit 240 extracts the noise signal by passing low frequency components therethrough.

A method of measuring biological signals according to various embodiments of the present invention will be described below.

Biological signals obtained using the principle of a Doppler radar include a heartbeat signal, a breathing signal, and noise signals attributable to other motions. If the noise signals attributable to other motions are eliminated using a suitable compensation method, more accurate heartbeat and breathing signals can be obtained. That is, at the time of measuring the heartbeat and breathing, the method of compensating for noise signals attributable to motions is configured in such a way that, when the first signal output through the division of power in the radar system 100 is transmitted to the heart of the target body, is reflected from the heart, and is then received through the reception antenna 132, biological signals including the heartbeat, the breathing, noise attributable to the motion of the human body, etc., can be obtained if a carrier frequency component is eliminated from the Doppler-converted signal using the second signal output from the coupler 120 through the division of the power, and in such a way that more accurate biological information can be extracted by eliminating using the combiner 300 the noise signal, which is extracted by the optical system 200 as a result of the motion of the target body, from the signal output from the mixer 150.

Therefore, since the radar realizes a Doppler effect based on the motion of the heart and lung by reaching the exterior of the human body and penetrating into even the interior of the body, and the light source reacts only to external motions, the noise signal attributable to the motion of the target body can be compensated for if a light source signal is subtracted from a radar signal, thus extracting accurate heartbeat and breathing signals.

Figure 4:
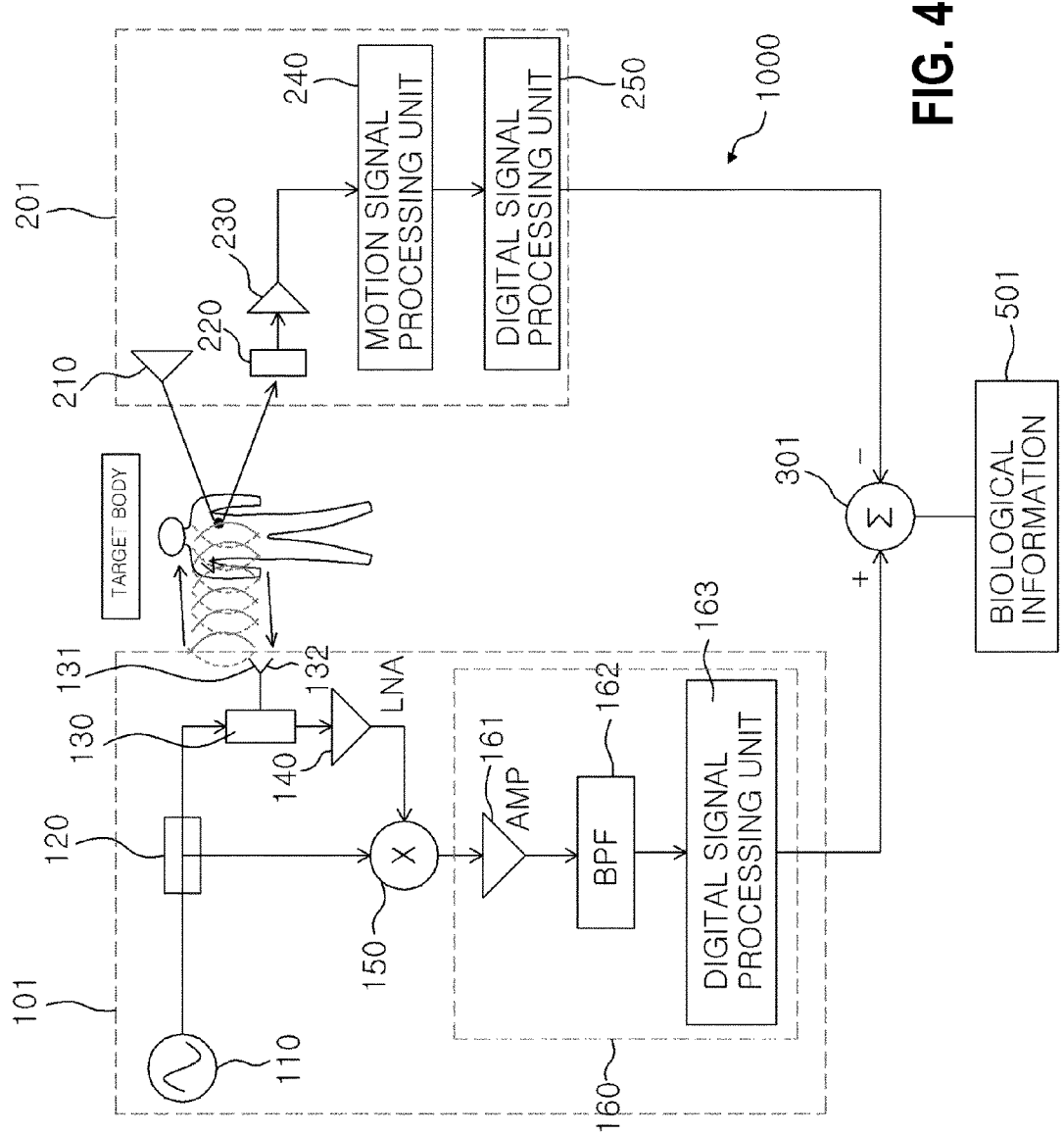
FIG. 4 is a block diagram showing another embodiment of the heart rate monitor of a drowsiness detection apparatus.

FIG. 4 is a block diagram showing another embodiment of the heart rate monitor of the drowsiness detection apparatus.

As shown in FIG. 4, a heart rate monitor 1000 includes a radar system 101 and an optical system 201, and further includes a combiner 301 for eliminating a noise signal, which is extracted and output from the optical system 201, from the output signal of the radar system 101, and a biological signal recognition unit 501 for obtaining biological signals from the combiner 301.

Hereinafter, the components and functions of the radar system 101 and the optical system 201 will be described in detail.

The radar system 101 includes a signal generator 110, a coupler 120, a transmission/reception converter 130, a low-noise amplifier 140, a mixer 150, and a signal processing unit 160.

First, the signal generator 110 generates and outputs specific frequency signals.

The coupler 120 receives the signals generated by the signal generator 110, divides the signals into a second signal which is a reference frequency signal and a first signal which is to be radiated to the heart of the target body, and then outputs the first and second signals. At this time, the first and second signals may be divided at a predetermined ratio, for example, a ratio of 50:50.

The transmission/reception converter 130 includes a transmission antenna 131 for receiving the first signal from the coupler 120 and radiating the first signal to the heart of the target body, and a reception antenna 132 for receiving a reflected wave which is returned from the heart of the target body after the first signal has been transmitted through the transmission antenna 131 and has been incident on the heart of the target body.

The low-noise amplifier 140 amplifies the signal received through the reception antenna 132.

The mixer 150 mixes the second signal output from the coupler 120 with the signal amplified by the low-noise amplifier 140, and outputs the mixed signal.

The signal processing unit 160 amplifies the signal output from the mixer 150 using an amplifier 161, detects a heartbeat signal and a breathing signal by performing filtering using a band pass filter 162, and converts the heartbeat signal and the breathing signal into digital signals and outputs the digital signals using a digital signal processing unit 163.

The optical system 201 includes a light source unit 210, a photodetection unit 230, a motion signal processing unit 240, and a digital signal processing unit 250.

In this case, the optical system 201 may further include a filter unit 220 which allows only light, having a specific wavelength and a predetermined light source bandwidth, to pass therethrough.

The light source unit 220 includes a light source for generating light and a light transmission optical system for radiating light to the heart region of the target body.

In this case, the light source may be a fluorescent lamp and is not limited to a specific type, but may be preferably implemented using an LED or LD, and may preferably use visible, infrared or ultraviolet rays.

Further, the light transmission optical system may be implemented as one system or may be arranged in the form of an array.

Further, light is preferably radiated to a portion having an area similar to the area of the heart region of the target body to which the signal is radiated by the transmission antenna 131 of the radar system 101.

The photodetection unit 240 includes a light reception optical system for detecting a light signal reflected from the target body after being radiated from the light source unit 220. At this time, the filter unit 230 which allows only light, having a specific wavelength and a predetermined light source bandwidth, to pass therethrough is preferably arranged upstream of the photodetection unit 240. In this case, the light source bandwidth is preferably less than 100 nm.

The motion signal processing unit 250 extracts a noise signal attributable to the motion of the target body from the signal detected by the photodetection unit 240. In this case, the motion signal processing unit 250 extracts the noise signal by passing low frequency components therethrough.

The digital signal processing unit 260 converts the noise signal extracted by the motion signal processing unit 250 into a digital signal, and outputs the digital signal.

When an additional description is made with regard to the above embodiments of the present invention, FIG. 2 shows the embodiment configured such that, after electrical signals from the radar system 100 and the optical system 200 are mixed with each other using hardware, signals such as a heartbeat signal and a breathing signal are extracted through suitable signal processing, whereas FIG. 3 shows the embodiment configured such that signals from the radar system 101 and the optical system 201 are separately processed, and a noise signal attributable to motion, output from the optical system 201, is processed using software, and thus accurate heartbeat and breathing signals from which the motion of the human body is eliminated are extracted.

The drowsiness detection method of the present invention is configured such that the heart rate monitor 1000 measures a heartbeat once for each time period (per minute), and outputs a warning sound, voice message or vibration through the output unit 4000 in the case where a value, obtained by subtracting a counted value monitored one minute before the current time from a counted value monitored two minutes before the current time through the processing of the central processing unit 3000, falls within a range from 2 to 10 or from −2 to −10, and where, with the passage of time, the value falling within the range from 2 to 10 or from −2 to −10 is successively detected from two to ten times within the same range. That is, a description will be made as follows when the counted value monitored two minutes before the current time is defined as "t2", the counted value monitored one minute before the current time is defined as "t1", and a value within the range is defined as "a".

If a value of "t2−t1" is "a", and the value "a" is successively measured for the next time period (i.e., a minute) through the processing of the central processing unit 3000, the warning sound, voice message or vibration is output through the output unit 4000.

Hereinafter, a drowsiness detection method according to various embodiments of the present invention will be described in detail.

First, a heartbeat signal and a breathing signal are detected, without making direct contact with a target body, by exploiting together a scheme which uses the principle of a Doppler radar and an optical system scheme which uses a light source/photodetector so that a heartbeat can be detected even when a human body is moving.

In this case, the optical system further includes a filter unit which is arranged upstream of the photodetection unit and configured to allow only light, having a specific wavelength and a predetermined light source bandwidth, to pass therethrough. Further, the light source bandwidth is preferably less than 100 nm.

Here, the light source is implemented using an LED or LD. Further, the light source uses visible, infrared or ultraviolet rays.

Next, respective signals detected by the scheme using the principle of the Doppler radar and the optical system scheme using the light source/photodetector are individually applied to the amplification unit, so that noise signals are eliminated from the respective signals and the noise-free signals are amplified.

Next, the signals output at the second step are applied to the central processing unit, so that signal processing is performed on the signals, and the processed signals are combined.

Next, the value output at the third step is counted, and a warning sound, voice message or vibration is output through the output unit in the case where a value obtained by subtracting a counted output value which was monitored one minute before the current time, from a counted output value which was monitored two minutes before the current time, falls within a range from 2 to 10, or from −2 to −10 and where, with the passage of time, the value falling within the range from 2 to 10 or from −2 to −10 is successively detected from two to ten times within the same range.

Therefore, the drowsiness detection method may successively measure the heart rate and the number of breaths of a user, count a normal heart rate, compare the counted value with a counted value, obtained when a heart rate and the number of breaths are reduced due to the occurrence of drowsiness, through subtraction, and provide a warning sound, voice message or vibration to the user when the user is determined to be drowsy. Further, various embodiments of the present invention are advantageous in that they sense using the heart rate monitor a phenomenon in which, when the user drowses off, the heart rate is slowed and the number of breaths decreases, and in that it causes the user who is drowsing off to return to an alert state by generating the warning sound or vibration, thus preventing accidents attributable to drowsy driving from occurring.

Although the preferred embodiments of the present invention have been described based on limited embodiments and drawings, those skilled in the art will appreciate that the present invention is not limited to the embodiments and drawings, and various changes and modifications are possible, without departing from the scope and spirit of the invention as disclosed in the accompanying claims and equivalents thereof.

At the present time in which the number of vehicles is gradually increasing, drunk driving and drowsy driving are the principal causes of vehicular accidents which greatly influence human lives. The present invention provides a drowsiness detection method, which successively measures the heart rate and the number of breaths of a user, counts a normal heart rate, compares the counted value with a counted value, obtained when the heart rate and the number of breaths are reduced due to the occurrence of drowsiness, through subtraction, and notifies the user of any danger by generating a warning sound, voice message or vibration when the user is determined to be drowsy, thus enabling detection apparatuses to be produced using various components and to be universally used.

TABLE OF REFERENCE CHARACTERS 100, 101 radar system
110 signal generator
120 coupler
130 transmission/reception converter
131 transmission antenna
132 reception antenna
140 low-noise amplifier
150 mixer
160, 400 first and second signal processing units
161, 410 first and second amplifiers
162, 420 first and second band pass filters
163, 430 first and second digital signal processing units
200, 201 optical system
210 light source unit
220 filter unit
230 photodetection unit
240 motion signal processing unit
250 digital signal processing unit
300, 301 first and second combiners
500, 501 first and second biological signal recognition units
1000 heart rate monitor
2000 amplification unit
3000 central processing unit
4000 output unit

The invention claimed is:

1. A drowsiness detection method, comprising:
   a first step of detecting a heartbeat signal and a breathing signal without making direct contact with a target body by exploiting together a scheme using a principle of a Doppler radar and an optical system scheme using a light source/photodetector so that a heartbeat can be detected when a human body is moving;
   a second step of applying the signals, detected by the scheme using the principle of the Doppler radar and the optical system scheme using the light source/photodetector to respective amplification units, eliminating noise signals from the detected signals, respectively, and amplifying noise-free signals;
   a third step of applying signals output at the second step to a central processing unit, performing signal processing on the signals, and combining respective processed signals; and
   a fourth step of counting an output value output at the third step, and outputting a warning sound, voice message or vibration through an output unit in a case where a value, obtained by subtracting a counted output value which was monitored one minute before a current time, from a counted output value which was monitored two minutes before the current time, falls within a range from 2 to 10, or from −2 to −10 and where, with a passage of time, the value falling within the range from 2 to 10 or from −2 to −10 is successively detected from two to ten times within a same range.

2. The drowsiness detection method according to claim 1, wherein the optical system comprises a filter unit arranged upstream of a photodetection unit and configured to allow only light, having a specific wavelength and a predetermined light source bandwidth, to pass therethrough.

3. The drowsiness detection method according to claim 2, wherein the light source bandwidth is less than 100 nm.

4. The drowsiness detection method according to claim 2, wherein the light source is implemented using a Light Emitting Diode (LED) or a Laser Diode (LD).

5. The drowsiness detection method according to claim 2, wherein the light source uses visible, infrared or ultraviolet rays.

6. The drowsiness detection method according to claim 1, wherein the light source is implemented using a Light Emitting Diode (LED) or a Laser Diode (LD).

7. The drowsiness detection method according to claim 1, wherein the light source uses visible, infrared or ultraviolet rays.

8. A drowsiness detection system, comprising:

a heart rate monitor including a radar system and an optical system, an amplification unit, a central processing unit and an output unit, wherein the radar system comprises:

a signal generator for generating specific frequency signals;

a coupler for receiving the signals generated by the signal generator and dividing a second signal, which is a reference frequency signal, and a first signal to be radiated to a heart of a target body, and outputting the first and second signals;

a transmission antenna for receiving the first signal from the coupler and radiating the first signal to the heart of the target body;

a reception antenna for receiving a reflected wave which is returned from the heart of the target body after the first signal has been transmitted through the transmission antenna and has been incident on the heart of the target body;

a low-noise amplifier for amplifying a signal received through the reception antenna;

a mixer for mixing the second signal output from the coupler with the signal amplified by the low-noise amplifier; and a signal processing unit for amplifying a signal output from the mixer, filtering the amplified signal, converting the filtered signal into a digital signal, and outputting the digital signal, and wherein the optical system comprises:

a light source unit including a light source for generating light and a light transmission optical system for radiating light to a portion identical to a heart region of the target body to which the signal is radiated by the transmission antenna of the radar system;

a photodetection unit including a light reception optical system for detecting a light signal reflected from the target body after being radiated to the target body;

a motion signal processing unit for extracting a noise signal attributable to a motion of the target body from the signal detected by the photodetection unit; and a digital signal processing unit for converting the noise signal extracted by the motion signal processing unit into a digital signal and outputting the digital signal, wherein the heart rate monitor further comprises:

a combiner for eliminating the noise signal output from the digital signal processing unit of the optical system from the signal output from the signal processing unit of the radar system; and a biological signal recognition unit for obtaining biological signals from the combiner, wherein the amplification unit receives signals respectively detected by a scheme using a principle of the Doppler radar and a scheme of the optical system using the light source/photodetector, eliminates noise signals from the detected signals, respectively, and amplifies the noise-free signals, and wherein the central processing unit individually receives signals output from the amplification unit, performs signal processing on the signals, combines the processed signals with each other, counts each of values output from the amplification unit, monitors the output value, and outputs a warning sound, voice message or vibration through the output unit if it is determined as a result of the monitoring that the output value falls within a detection range.

9. The drowsiness detection system according to claim 8, wherein the detection range is a range in which a value, obtained by subtracting a counted output value which was monitored one minute before a current time from a counted output value which was monitored two minutes before the current time through processing of the central processing unit which counts the output value, falls within a range of 2 to 10 and in which the value falling within the range from 2 to 10 is successively detected from two to ten times with passage of time.

10. The drowsiness detection system according to claim 9, wherein the light source is implemented using a Light Emitting Diode (LED) or a Laser Diode (LD).

11. The drowsiness detection system according to claim 9, wherein the light source uses visible, infrared or ultraviolet rays.

12. The drowsiness detection system according to claim 8, wherein the optical system further comprises a filter unit arranged upstream of the photodetection unit and configured to allow only light, having a specific wavelength and a predetermined light source bandwidth, to pass therethrough.

13. The drowsiness detection system according to claim 12, wherein the light source bandwidth is less than 100 nm.

14. The drowsiness detection system according to claim 12, wherein the light source is implemented using a Light Emitting Diode (LED) or a Laser Diode (LD).

15. The drowsiness detection system according to claim 12, wherein the light source uses visible, infrared or ultraviolet rays.

* * * * *